United States Patent
Mueth et al.

(10) Patent No.: US 7,150,834 B2
(45) Date of Patent: Dec. 19, 2006

(54) MULTIPLE LAMINAR FLOW-BASED RATE ZONAL OR ISOPYCNIC SEPARATION WITH HOLOGRAPHIC OPTICAL TRAPPING OF BLOOD CELLS AND OTHER STATIC COMPONENTS

(75) Inventors: Daniel M. Mueth, Chicago, IL (US); Amy Anderson, Prospect Heights, IL (US); Jessica Shireman, Kansas City, MO (US)

(73) Assignee: Arryx, Inc., Chicago, IL (US)

( * ) Notice: Subject to any disclaimer, the term of this patent is extended or adjusted under 35 U.S.C. 154(b) by 54 days.

(21) Appl. No.: 10/867,328

(22) Filed: Jun. 13, 2004

(65) Prior Publication Data

US 2005/0061962 A1    Mar. 24, 2005

Related U.S. Application Data

(63) Continuation-in-part of application No. 10/630,904, filed on Jul. 31, 2003.

(51) Int. Cl.
B01D 21/01 (2006.01)

(52) U.S. Cl. ............ 210/732; 210/800; 210/802; 210/927; 435/173.1; 422/72; 422/82.05; 422/101; 436/177

(58) Field of Classification Search ........... 250/251; 435/173.1; 210/732, 800, 802, 804, 927; 436/177; 422/82.05, 72, 101
See application file for complete search history.

(56) References Cited

U.S. PATENT DOCUMENTS

| | | | | | |
|---|---|---|---|---|---|
| 4,409,106 | A | * | 10/1983 | Furuta et al. | 210/732 |
| 4,424,132 | A | * | 1/1984 | Iriguchi | 210/800 |
| 6,815,664 | B1 | * | 11/2004 | Wang et al. | 250/251 |
| 6,833,542 | B1 | * | 12/2004 | Wang et al. | 250/251 |

* cited by examiner

*Primary Examiner*—Kiet T. Nguyen
(74) *Attorney, Agent, or Firm*—Jean C. Edwards, Esq.; Akerman Senterfitt

(57) ABSTRACT

The invention provides a method and apparatus for separating blood into components, may be expanded to include other types of cellular components, and can be combined with holographic optical manipulation or other forms of optical tweezing. One of the exemplary methods includes providing a first flow having a plurality of blood components; providing a second flow; contacting the first flow with the second flow to provide a first separation region; and differentially sedimenting a first blood cellular component of the plurality of blood components into the second flow while concurrently maintaining a second blood cellular component of the plurality of blood components in the first flow. The second flow having the first blood cellular component is then differentially removed from the first flow having the second blood cellular component. Holographic optical traps may also be utilized in conjunction with the various flows to move selected components from one flow to another, as part of or in addition to a separation stage.

6 Claims, 7 Drawing Sheets

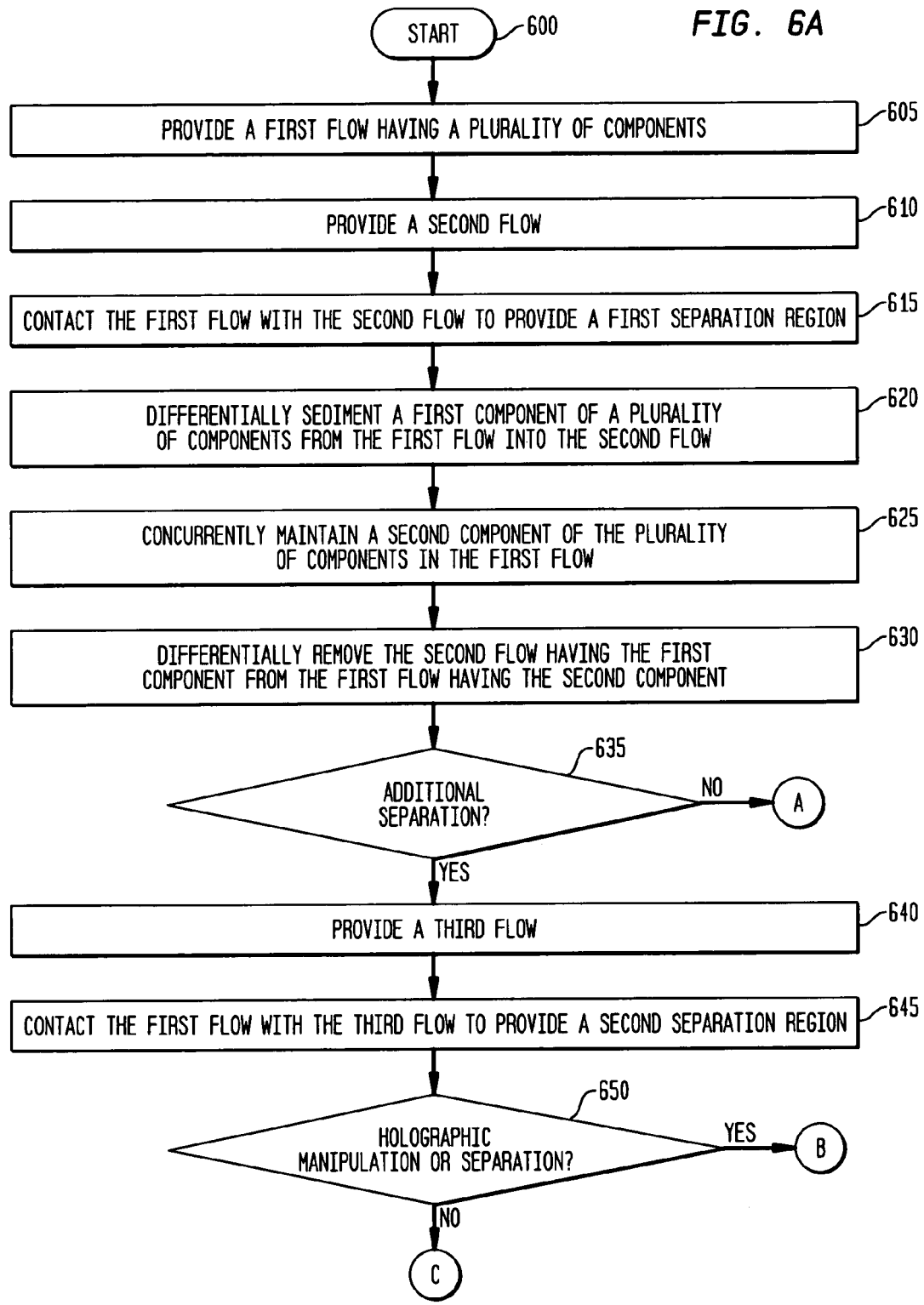

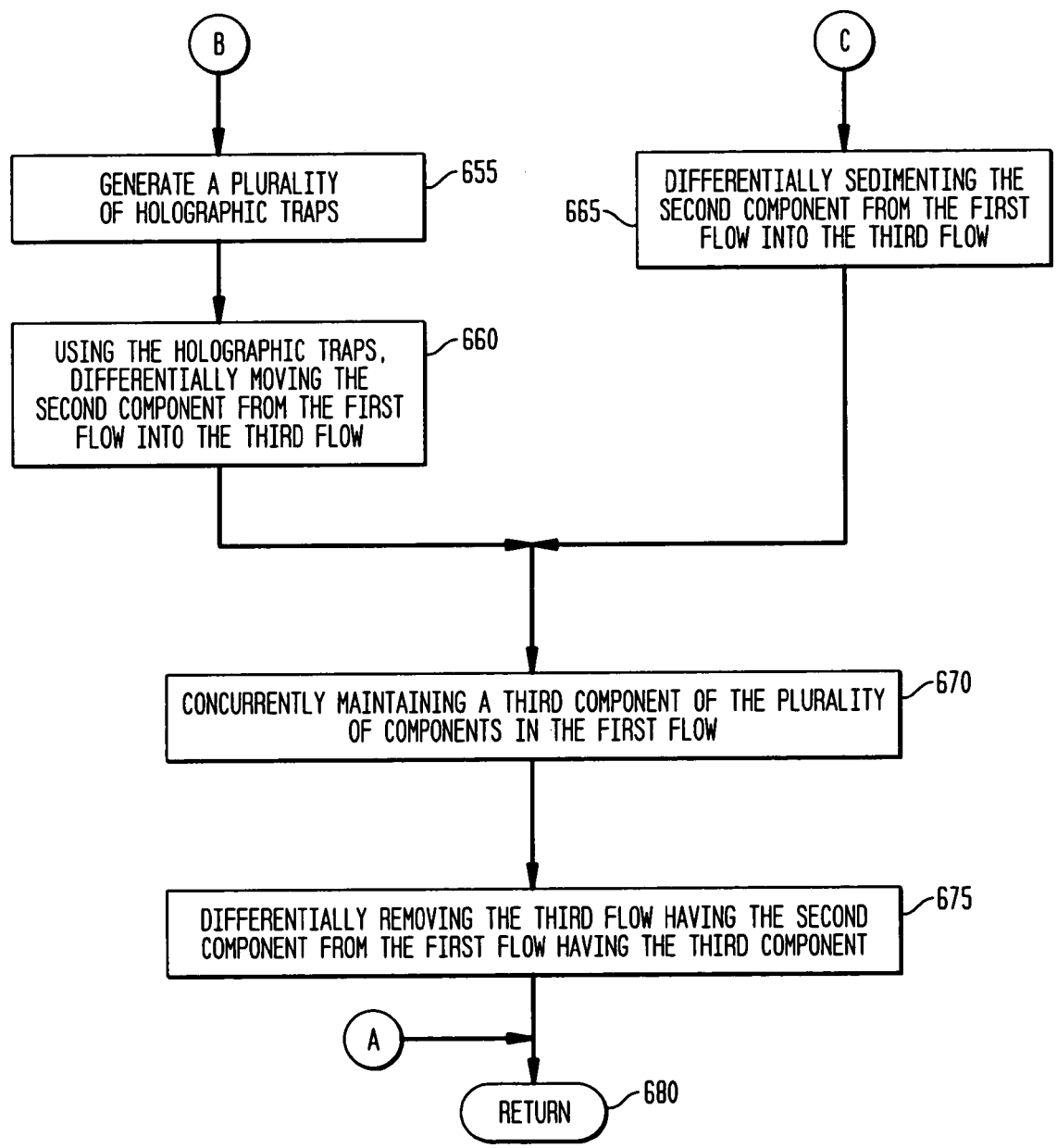

MULTIPLE LAMINAR FLOW-BASED RATE ZONAL OR ISOPYCNIC SEPARATION WITH HOLOGRAPHIC OPTICAL TRAPPING OF BLOOD CELLS AND OTHER STATIC COMPONENTS

CROSS-REFERENCE TO RELATED APPLICATIONS

The present invention is a Continuation-In-Part Application of Lewis Gruber et al., U.S. patent application Ser. No. 10/630,904, filed Jul. 31, 2003, entitled "SYSTEM AND METHOD OF SORTING MATERIALS USING HOLOGRAPHIC LASER STEERING," commonly assigned herewith, the contents of which are incorporated y reference herein, with priority claimed for all commonly disclosed subject matter (the "first related application").

FIELD OF THE INVENTION

The present invention relates generally to techniques and systems for separation of cellular materials such as blood into its various cellular components and fractions, such as platelets, and more particularly, to a separation of blood or other biological materials into cellular components or other static components using multiple laminar flows and rate zonal or isopycnic separation, which further may be coupled with holographic optical trapping and manipulation.

BACKGROUND OF THE INVENTION

There are several categories of blood cells. Erythrocyte or red blood cell (RBC) counts are for women 4.8 million cells/$\mu$l and men 5.4 million cells/$\mu$l. RBCs make up 93% of the solid element in blood and about 42% of blood volume. Platelets are 2 $\mu$m–3 $\mu$m in size. They represent 7% of the solid elements in blood and about 3% of the blood volume, corresponding to about 1.5 to $4 \times 10^{11}$ cells per liter. There are 5 general types of white blood cells (WBCs) or leukocytes accounting for about 1.5 to $4 \times 10^9$ cells per liter. The WBCs comprise: 50–70% Neutrophils (12–15 $\mu$m in size); 2–4% Eosinophils (12–15 $\mu$m in size); 0.5–1% Basophils (9–10 $\mu$m in size); 20–40% Lymphocytes (25% B-cells and 75% T-cells) (8–10 $\mu$m in size); and 3–8% Monocytes (16–20 $\mu$min size). They comprise 0.16% of the solid elements in the blood, and approximately 0.1% of the blood volume corresponding to around 4 to $12 \times 10^9$ per liter. A subject with an infection might have a WBC count as high as $25 \times 10^9$ per liter.

Platelets are the smallest cells in the blood and are important for releasing proteins into the blood that are involved in clotting. Patients with immune diseases that cause lower counts (such as cancer, leukemia and other chemotherapy patients) sometimes need platelet transfusions to prevent their counts from becoming too low. The platelet count in adults is normally between 140,000–440,000 cells/$\mu$l, and this number should not fall below 50,000 cells/$\mu$L because platelets play an integral role in blood clotting.

Blood separation techniques have traditionally employed discrete centrifugation processes. More particularly, a certain volume of blood is removed from a donor at a particular time. That volume of blood is then subjected to different levels of centrifugation to provide corresponding blood fractions for blood components such as plasma, platelets, red blood cells, and white blood cells. This process is discrete, rather than continuous, such that if more blood from the donor is to be processed, another volume is removed from the donor, and the process is repeated.

The steps in platelet collection are: collection of blood from donor: addition of anticoagulant; separation via centrifugation; return of red cells, leukocytes and plasma to the donor. A collection normally contains about 200–400 ml of plasma, which is reduced to avoid imcompatibility. This collection normally contains about 8 to $8.5 \times 10^{10}$ platelets. A donor normally gives approximately 10% of his/her platelets with no loss in clotting ability, although a larger number of platelets could be separated from the blood. These platelets must be used within five days of collection.

Plateletpheresis, called apheresis, is a state of the art process by which platelets are separated [Haemonetics Component Collection System (CCS) and Multi Component System (Multi)(Haemonetics, Braintree, Mass.)]. This automated machine separates platelets from blood over a period of 1.5 to 2 hours (assuming 10% donation). This process is faster than traditional approaches and is completely automated and can be used for single or double platelet doses. Nevertheless, the process is slow relative to the patience of donors and is capable of improvement for the purity of the separated platelet fraction.

Other procedures are also time consuming, often taking several hours, particularly when unused blood fractions are to be returned to the donor. For example, platelet donation make take several hours, as whole blood is removed from the donor, fractionated through centrifugation to obtain the platelets, and the remaining blood components are then injected back into the donor. This centrifugation process is also comparatively harsh, also can result in damage to a proportion of the harvested cells, effectively reducing the usable yield of the blood fractions.

As a consequence, a need remains for a blood separation technique and apparatus which is continuous, has high throughput, provides time saving, and which causes negligible or minimal damage to the various blood components. In addition, such techniques should have further applicability to other biological or medical areas, such as for separations of cellular, viral, cell organelle, globular structures, colloidal suspensions, and other biological materials.

SUMMARY OF THE INVENTION

The exemplary embodiments of the present invention provide for separating components in a mixture, such as separating the various blood components of whole blood into corresponding fractions, such as a platelet fraction, a red blood cell fraction, a white blood cell fraction, and a plasma fraction. The various embodiments of the present invention provide separation of components on a continuous basis, such as within a continuous, closed system, without the potential damage and contamination of prior art methods, particularly for fractionation of blood components. The continuous process of the present invention also provides significant time savings and higher throughput for blood fractionation. In addition, the various embodiments may also include additional means for separating and manipulating the components, particularly holographic optical manipulation and separation.

An exemplary method of separating blood into components includes providing a first flow having a plurality of blood components; providing a second flow; contacting the first flow with the second flow to provide a first separation region; and differentially sedimenting a first blood cellular component of the plurality of blood components into the second flow while concurrently maintaining a second blood cellular component of the plurality of blood components in the first flow. The second flow having the first blood cellular component is then differentially removed from the first flow having the second blood cellular component.

The various sedimentation steps of the present invention may be rate zonal or isopycnic. In addition, the first flow and the second flow are substantially non-turbulent, and may also be substantially laminar.

In a selected embodiment, the first blood cellular component is a plurality of red blood cells and a plurality of white blood cells, and the second blood cellular component is a plurality of platelets. For the first blood cellular component, the plurality of white blood cells may be holographically separated from the plurality of red blood cells. Other holographic manipulations of the present invention include holographically removing a plurality of contaminants from the first flow, holographically separating biological debris from the first flow, and holographically separating a plurality of second blood cellular components from the first flow.

Additional separation stages may also be included, with the exemplary method providing a third flow; contacting the first flow with the third flow to provide a second separation region; and differentially sedimenting the second blood cellular component of the plurality of blood components to sediment into the third flow while concurrently maintaining a third blood component of the plurality of blood components in the first flow. In selected embodiments, the second blood cellular component is a plurality of platelets and wherein the third blood component is plasma.

A second exemplary method of separating a fluid mixture into constituent, non-motile components, in accordance with the present invention, includes: providing a substantially laminar first flow having the fluid mixture, the fluid mixture having a plurality of components, the plurality of components having a corresponding plurality of sedimentation rates; providing a substantially laminar second flow; contacting the first flow with the second flow to provide a first separation region, the first flow and the second flow having a substantially non-turbulent interface within the separation region; differentially sedimenting from the first flow a first component of the plurality of components into the second flow to form an enriched second flow and a depleted first flow, while concurrently maintaining a second component of the plurality of components in the first flow, the first component having a first sedimentation rate of the plurality of sedimentation rates and the second component having a second sedimentation rate of the plurality of sedimentation rates, wherein the first sedimentation rate is comparatively greater than the second sedimentation rate; differentially removing the enriched second flow from the depleted first flow; and holographically manipulating the second component in the depleted first flow.

The second exemplary method may also include additional separation stages, such as a holographic separation, including: providing a third flow; contacting the depleted first flow with the third flow to provide a second separation region; and holographically trapping the second component and moving the second component from the depleted first flow into the third flow while concurrently maintaining a third component of the plurality of components in the depleted first flow.

An exemplary apparatus embodiment of the invention for separating a fluid mixture into constituent, non-motile components includes: a first sorting channel having a first inlet for a first flow and a second inlet for a second flow; the first sorting channel further having a first outlet for the first flow and a second outlet for the second flow, the first sorting channel further having means to maintain the first flow and second flow substantially non-turbulent, the first sorting channel adapted to allow a first component in the first flow, of a plurality of components in the first flow, to sediment into the second flow to form an enriched second flow and a depleted first flow, while concurrently maintaining a second component of the plurality of components in the first flow; a second, optically transparent sorting channel having a first optical inlet coupled to the first outlet for the first flow and having a first optical outlet, the second, optically transparent sorting channel further having a second optical inlet for a third flow and a second optical outlet for the third flow; and a holographic optical trap coupled to the second, optically transparent sorting channel, the holographic optical trap adapted to generate a holographic optical trap to select and move the second component from the first flow into the third flow.

Another apparatus or system for separating a plurality of components in a fluid comprises: an optically transparent sorting channel having a first inlet for a first flow and a second inlet for a second flow, the optically transparent sorting channel further having a first outlet for the first flow and a second outlet for the second flow; and a holographic optical trap system coupled to the optically transparent sorting channel, the holographic optical trap system adapted to generate a holographic optical trap to select and move a first component in the first flow, of a plurality of components in the first flow, into the second flow to form an enriched second flow and a depleted first flow, while a second component of the plurality of components is concurrently maintained in the first flow.

Another method embodiment provides for separating a plurality of cells, comprising: providing a first flow having the plurality of cells; providing a second flow; contacting the first flow with the second flow to provide a first separation region; and differentially sedimenting a first cell of the plurality of cells into the second flow while concurrently maintaining a second cell of the plurality of cells in the first flow. The method generally also includes differentially removing the second flow having the first cell from the first flow having the second cell. The method may also provide for providing a third flow; contacting the first flow with the third flow to provide a second separation region; and differentially sedimenting the second cell of the plurality of cells into the third flow while concurrently maintaining a third cell of the plurality of cells in the first flow. In addition, a plurality of second cells may be holographically separated from the first flow, and a plurality of contaminants or biological debris may be holographically removed from the first flow.

Numerous other advantages and features of the present invention will become readily apparent from the following detailed description of the invention and the embodiments thereof, from the claims and from the accompanying drawings.

BRIEF DESCRIPTION OF THE DRAWINGS

The objects, features and advantages of the present invention will be more readily appreciated upon reference to the following disclosure when considered in conjunction with the accompanying drawings, in which:

FIG. 6 (divided into FIG. 6A and FIG. 6B) is a flow diagram illustrating a method embodiment of the present invention.

DETAILED DESCRIPTION OF THE EXEMPLARY EMBODIMENTS

Figure 1:
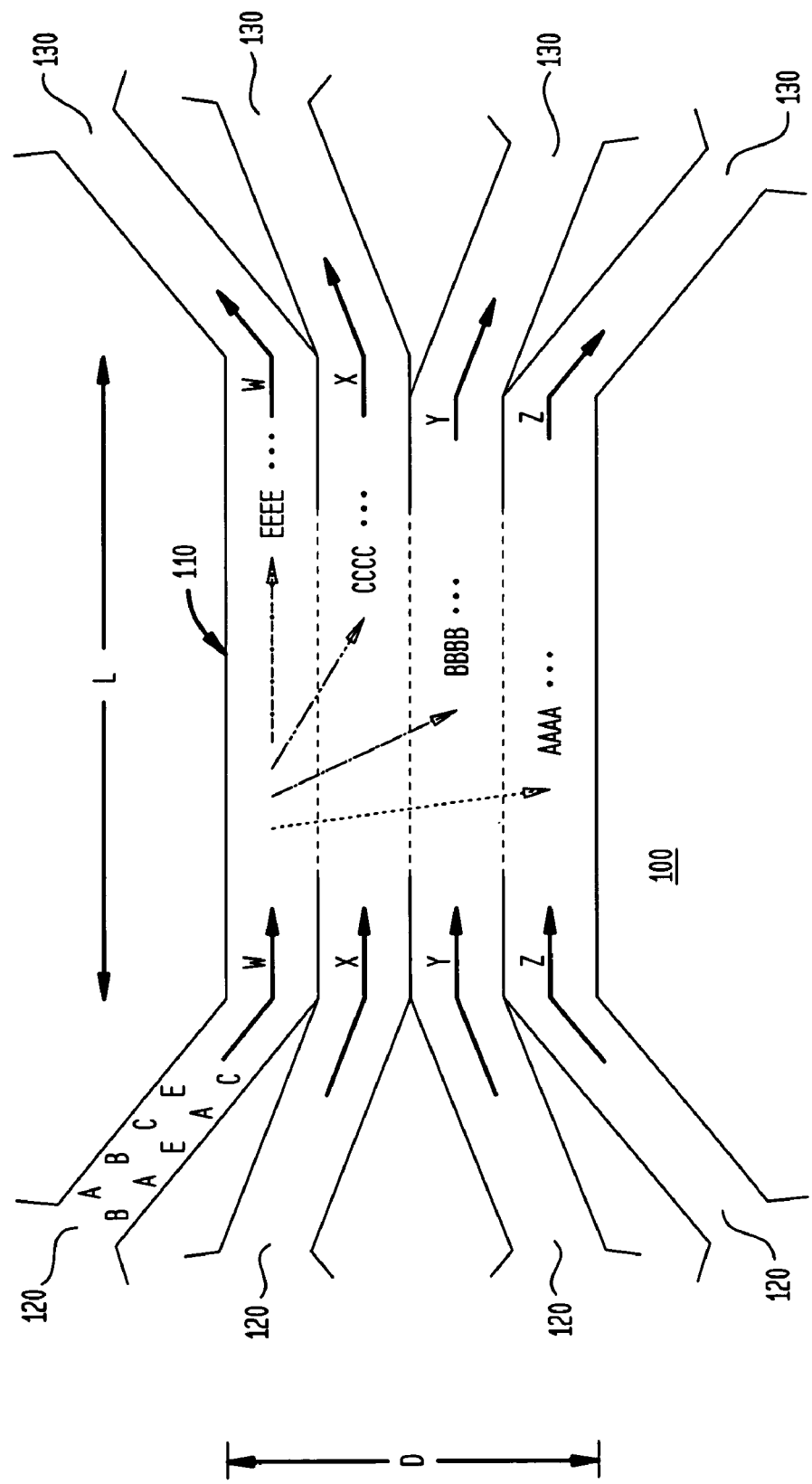
FIG. 1 is a lateral view of an apparatus 100 in accordance with the present invention.

While the present invention is susceptible of embodiment in many different forms, there are shown in the drawings and will be described herein in detail specific embodiments thereof, with the understanding that the present disclosure is to be considered as an exemplification of the principles of the invention and is not intended to limit the invention to the specific embodiments illustrated.

As indicated above, the various embodiments of the present invention provide for separating components in a mixture, such as separating the various blood components of whole blood into corresponding fractions, such as a platelet fraction, a red blood cell fraction, a white blood cell fraction, and a plasma fraction. The various embodiments, as described below, utilize one or more sorting channels, having a plurality of substantially laminar flows, allowing one or more components to differentially sediment from one flow into another, thereby separating the components into corresponding flows. In addition, the various components may be sorted further using optical mechanisms, such as holographic optical trapping. The various embodiments of the present invention thereby provide separation of components on a continuous basis, such as within a continuous, closed system, without the potential damage and contamination of prior art methods, particularly for fractionation of blood components. The continuous process of the present invention also provides significant time savings for blood fractionation.

In addition to whole blood sorting and fractionation applications, the present invention is also suitable for other cell sorting applications, such as separations of cancer cells from normal or healthy cells in, for example, bone marrow extractions. The various embodiments of the present invention have further applicability to other biological or medical areas, such as for separations of cells, viruses, bacteria, cellular organelles or subparts, globular structures, colloidal suspensions, lipids and lipid globules, gels, immiscible particles, blastomeres, aggregations of cells, microorganisms, and other biological materials. For example, the component separation in accordance with the present invention may include cell "washing", in which contaminants (such as bacteria) are removed from cellular suspensions, which may be particularly useful in medical and food industry applications. Significantly, prior art flow-based techniques have not recognized any applicability to sorting or separation of non-motile cellular components using variable sedimentation rates and optical manipulation.

FIG. 1 is an illustration of a lateral view of an apparatus 100 in accordance with the present invention. As illustrated in FIG. 1, the sorting apparatus 100 includes a sorting channel 110, a plurality of inlets 120 and a plurality of outlets 130. A corresponding fluid flow, such as illustrated flows W, X, Y and Z, enters one of the inlets 120 and flows, substantially non-turbulently or otherwise as a laminar flow, across the sorting channel (or sorting region) 110, and out through a corresponding outlet 130, as illustrated.

The apparatus 100 (and 200, below) may be constructed of a plurality of materials, integrally or as discrete components, using a wide variety of materials, such as metals, ceramics, glass, and plastics. In selected embodiments, when coupled with holographic trapping or other form of optical tweezing, the apparatus 100 (or 200) is transparent to the selected wavelength of the holographic generator, such as optically transparent when the holographic generator utilizes visible wavelengths. Depending upon the selected application, the apparatus 100 (200) should also be sterile and may also have a controlled temperature. The various fluid flows may be fed into the inlets 120 through a wide variety of means known to those of skill in the art and are within the scope of the present invention, including use of peristaltic pumps or a gravity feed, for example, and such means may also be utilized to control the flow rates of the various flows W, X, Y and Z. When peristaltic pumps are utilized, to maintain a constant flow rate and pressure, bubble-traps may be incorporated at the inlets 120 of the apparatus 100 (or 200).

The various fluids utilized in the separation flows may be diluted or concentrated, to increase or decrease the volume of one of the solutions, or to impact the concentration of some dissolved or suspended material, or to impact physical properties of the solution such as its viscocity, temperature, or density. Examples for the apparatus 100, when used for blood sorting, include: (a) dilution of the blood to reduce clogging or hydrodynamic interaction between blood cells, (b) extension of the volume of the blood or a blood fraction, (c) modification of the density of the blood, a blood fraction, or another solution which impacts the flow properties or separation behavior, (d) extension of the volume of a solution to maintain in increase fluid volume, especially in circumstances when fluid volume is being removed from the system.

The various fluids utilized in the separation flows also may be "activated", such that some process is activated within the solution by some external influence or mixing with an external solution. Examples of external influences include: (a) applying an electric field, (b) applying a magnetic field, (c) exposing to light, (d) modifying the temperature, (e) introducing a chemical, (f) introducing a biological material, (g) shearing the solution, and (h) vibrating the solution. Examples of the activation which is caused by the external solution include: (a) alignment of particles, molecules, or cells, (b) polarization of one or more components of the solution, (c) cross-linking, (d) initiation or termination of chemical reaction, (e) initiation or termination of a biological response, (f) changing the type or rate of a chemical, physical, or biological response, or (g) causing a response or separation which depends upon the character of the particular component which is responding. Examples for the apparatus 100, when used for blood sorting, include: (a) addition of an agent to reduce clotting; (b) addition of agents to preserve viability or health of the blood solution or its components; (c) addition of agents which may augment the sorting process, such as by binding or collecting near certain components, thereby influencing one or more of their physical properties, including the addition of beads or other particles or polymers which may adhere to one or more species, and also including the introduction of salts or other materials which may influence the electrostatic interaction of materials or the hydrodynamic size or character of the materials; (d) addition of agents which may influence the flow properties, such as by changing the density, viscosity, surface tension, or other parameters; (e) addition of agents to enhance or suppress the aggregation of certain materials; and (f) addition of agents to enhance or suppress the adherence of certain materials to other materials or parts of the flow device.

In accordance with the invention, one of the fluid flows, such as the illustrated flow W, contains a plurality of components A, B, C and E. For example, when the fluid is whole blood, these components may be red blood cells ("RBC"), white blood cells ("WBC"), platelets, cellular debris and contaminants, all in plasma. Typically, many of the plurality of components have different sedimentation rates, typically measured using a Svedberg coefficient. For example, RBCs have a comparatively greater sedimentation rate than platelets, and will be expected to sediment faster on a passive basis, such as due to gravitational or buoyant forces, without the intervention of other, active mechanisms, such as centrifugation. As the various flows W, X, Y and Z flow through the sorting region 110, based upon different sedimentation rates, the plurality of components (such as cells or other particles) will sediment, moving from one flow to another. As illustrated, component A having the comparatively greatest sedimentation rate is illustrated as having moved from flow W to the lowest flow Z, component B having the comparatively next highest sedimentation rate is illustrated as having moved from flow W to the flow Y (above Z), component C having a comparatively smaller sedimentation rate is illustrated as having moved from flow W to the flow X (above Y), while component E having the comparatively smallest sedimentation rate, is illustrated as having remained in flow W (above Y). Using these different sedimentation properties, each of these components may be separated into a corresponding flow, and isolated from each other as each flow exits through its corresponding outlet 130. As each flow W, X, Y and Z exits through its corresponding outlet 130, that flow is differentially removed from the other flows, i.e., the flow is removed while the other flow remains intact or is otherwise separately removed from the remaining flows. In addition, this differential removal may be concurrent, namely, all flows removed concurrently or continuously.

Continuing to refer to FIG. 1, using whole blood with an anticoagulant (such as sodium citrate or heparin) as the fluid flow W, for example, the various blood fractions may be separated from each other, with red blood cells sedimenting fastest and represented by component A (e.g., 4.59 μm/s), white blood cells sedimenting at a slightly lower rate and represented by component B (e.g., 2.28 μm/s), platelets sedimenting at a comparatively slower rate and represented by component C (e.g., 0.055 μm/s), and plasma continuing to comprise flow W and represented by component E. Each blood fraction may then be removed through a corresponding outlet 130.

Not separately illustrated in FIG. 1, due to buoyant forces and relative density considerations, there may be particles or components in one or more of the fluid flows which will flow up to a higher flow (e.g., creaming). For example, less dense particles entering through flow X may rise into flow W, and exit with flow W through a corresponding outlet 130.

Illustrated in lateral view, the sorting channel (or sorting region) 110 of apparatus 11 has a varied length "L" parallel to the direction of flow, a depth "D" perpendicular to the direction of flow, and a width (not illustrated, extending into the page). These various dimensions may be selected based on a plurality of factors, particularly the flow rates and the sedimentation rates of the components of interest. For example, for a selected flow rate, the total length of the sorting channel should be long enough to differentially remove the component having the comparatively slowest sedimentation rate, illustrated as component C in FIG. 2, with shorter lengths corresponding to other flows for separation of components having faster sedimentation rates, as illustrated for flow Z having component A and flow Y having component B.

Flow rates may also vary between the plurality of flows utilized in apparatus 100. For example, higher flow rates in the lower level flows (such as Y and Z) may tend to compress the flows W and X, resulting in a shorter distance that certain components must traverse to sediment into the flows Y and Z.

In addition, the sedimentation of components through the various flows of the apparatus 100 is typically rate zonal, that is, based upon both relative density and size of the components to be separated, as well as the material's shape and electrostatic properties. Under other conditions, however, such as slower flow rates, thinner flow depths, and/or longer sorting channels 100, the sedimentation may also be isopycnic, that is, based only upon relative density of the components. When isopycnic separation is desired, the various fluids comprising the flows W, X, Y and Z may be selected and adjusted to create desired density gradients to match the component densities for the selected separations.

The various fluids comprising the generally laminar flows, such as flows W, X, Y and Z, may also be selected based on suitable criteria for the particular desired component separation. For example, for blood separation, the various flows may be comprised of whole blood, such as for flow W, and plasma or buffering solutions for the remaining flows. The various fluids may also be preprocessed prior to entry through the inlets 120, such as through dilution, addition of other components such as additives (such as anticoagulants, flocculants, or binding agents), viscosity or other flow property manipulation, or preprocessed through other separation techniques. Also for example, whole blood may be preprocessed to initially remove some red blood cells or to add an anticoagulant such as sodium citrate.

While illustrated with four flows or channels, it should be understood that the apparatus 100 (or 200, below) may be implemented with any number of flows and corresponding fluid inlets 120 and outlets 130. One limitation to the number of fluid flows is based on the ability to maintain each flow in a substantially laminar or non-turbulent manner, such that each interface between flows is substantially non-turbulent, to minimize any unwanted mixing of flows. In addition, there also may be relative density considerations for the fluids comprising the flows which could also result in limiting the number of flows utilized in a given stage of separation.

The various apparatus 100 (or 200, below) may be further coupled to additional apparatus 100 (200, below), in parallel for higher throughput, and in series for additional separation stages, such as for increased purity levels. In addition, the various apparatus 100 may also be combined with non-sedimentation separations, or be coupled in series with subsequent separations using non-sedimentation mechanisms, with additional separation of components between flows accomplished, for example, using optical forces such as holographic optical trapping of the first related application, incorporated herein by reference. These various apparatus 100, 200 or 300, moreover, may have different dimensions and different numbers of channels or flows.

Figure 2:
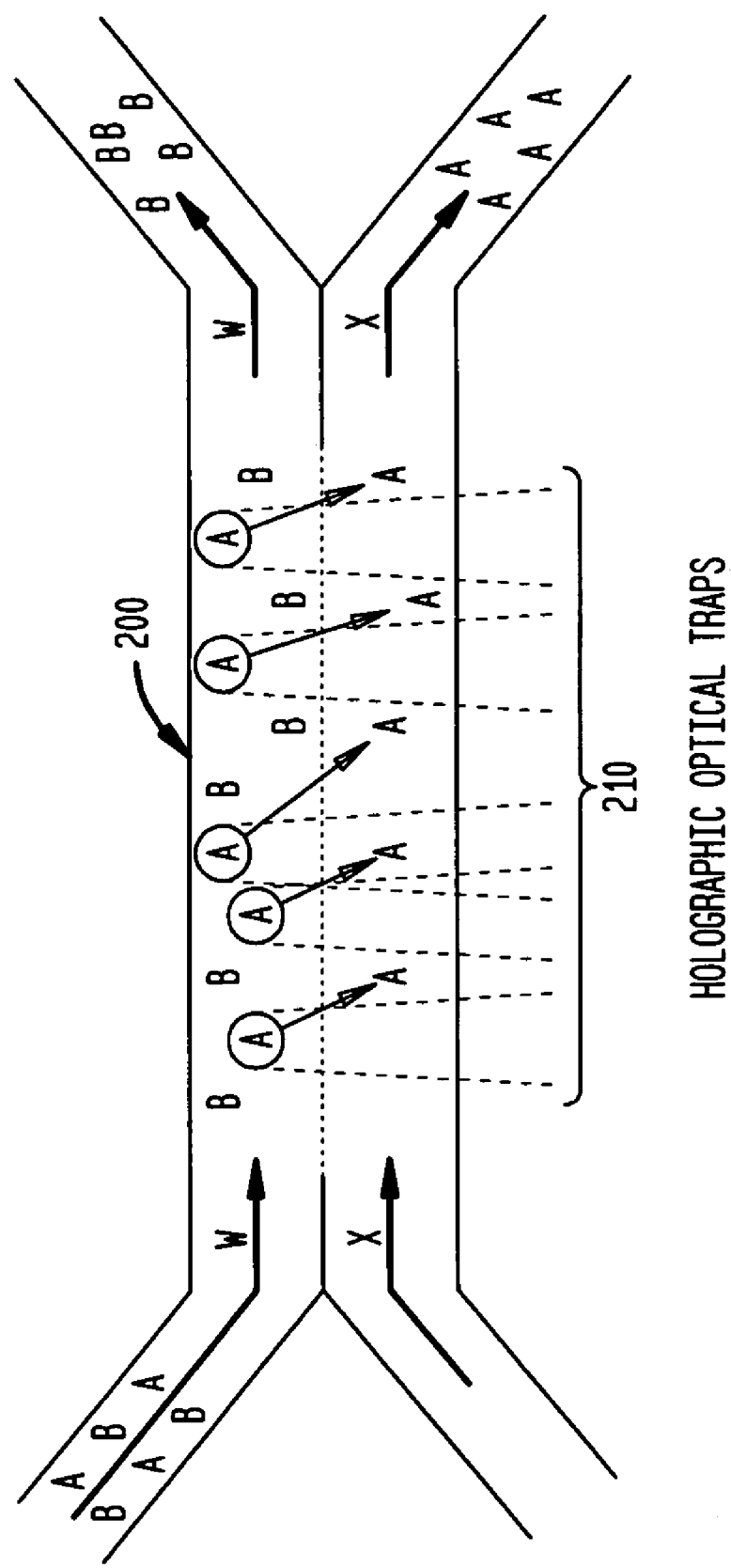
FIG. 2 is an illustration of optical trapping for component separation in an apparatus 200.

FIG. 2 is a general illustration of using such optical forces created by holographic or optical trapping for additional component separation in an apparatus 200. Creation and manipulation of the plurality of holographic optical traps 210 is explained in greater detail below with reference to FIGS. 4 and 5, with apparatus 200 forming the sample 506 of FIG. 5. Two flows W and X are illustrated in FIG. 2, with flow W initially having two components A and B. Holographic optical traps 210 (illustrated as conic sections in FIG. 2) are then utilized to capture "A" components, and move them into flow X. Such optical trapping is particularly useful for increased purification of a particular fraction, particularly for fractions having insufficient differentiation based on sedimentation rates. Such optical trapping is also particularly useful for removal of undesirable components, such as cellular debris and other impurities. In addition, where mixing or remixing of components may have occurred during the rate zonal laminar flow separations discussed above, the optical trapping may be particularly accurate in removing undesired components. For example, a comparatively small portion of white blood cells may not have sedimented fast enough, resulting in some white blood cell contamination of a platelet fraction. Optical trapping may be utilized to select and move the white blood cells into a separate flow, increasing the purity of the platelet fraction.

For blood sorting applications, it should be understood that platelets and RBC optically manipulate (or "tweeze") better than white blood cells. Using lower numerical apertures in the system 500 (discussed below), however, significantly improves optical manipulation of white blood cells.

When implemented in conjunction with optical traps, the apparatus 100, 200 or 300 should be embodied utilizing an optically transparent material, for the selected optical wavelength. When the holographic traps are implemented at other wavelengths, other correspondingly transparent materials may be utilized which are suitable for the selected wavelength. The apparatus 100, 200 or 300 is then implemented and placed in the location of the sample 506 illustrated in FIG. 5, with the system 500 utilized to perform the holographic optical trapping as one of or as part of a separation stage of the present invention.

Figure 3:
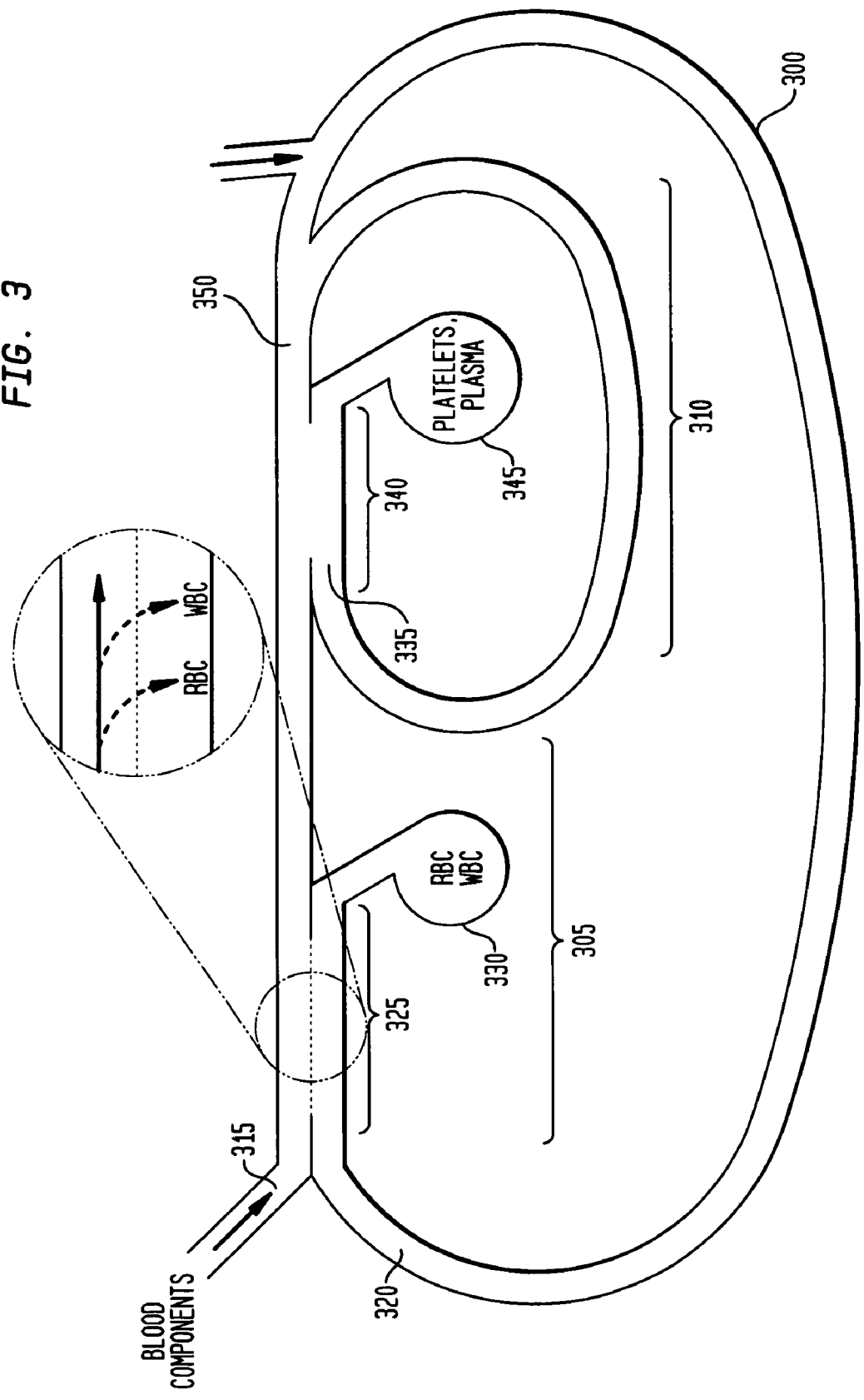
FIG. 3 is a diagram illustrating a closed, two-stage system 300 for blood component separation in accordance with the present invention.

FIG. 3 is a diagram illustrating a closed, two-stage system 300 for blood component separation in accordance with the present invention. In a first stage 305, blood components from a selected donor flow through inlet 315 to form a first flow, and plasma is returned (or primed on initial start up) through inlet 320 to form a second flow. The first and second flows are non-turbulent and otherwise laminar flows, and make non-turbulent contact with each other in first separation region 325, forming a non-turbulent interface region between the two flows. In the first separation region 325, both red blood cells and white blood cells sediment from the first flow into the second flow, and are collected in reservoir 330 for other uses (such as medical uses for packed cells) or for return to the selected donor. As indicated above, both the length of the first separation region 325 and the flow rate of the first flow are predetermined such that both red blood cells and white blood cells have sufficient time to passively sediment into the second flow, under gravitational and buoyant forces.

Continuing to refer to FIG. 3, the first flow, now substantially depleted of both red blood cells and white blood cells, flows non-turbulently on a continuous path into a second separation stage 310. In the second separation stage 310, the first flow enters a second separation region 340 with a third flow from inlet 335. The third flow is also comprised of plasma from the selected donor in the exemplary embodiment. In the second separation region 340, the platelets remaining in flow one passively sediment into flow three, and are collected with the plasma of flow three in reservoir 345 for medical use, for example. The further depleted flow one is then recirculated from outlet 350 back to inlets 320 and 335, to form the first and third flows, respectively. As indicated above, the system 300 may be primed with donor plasma at system start-up by, for example, centrifuging a portion of the selected donor's blood, or by initially using another biocompatible, non-toxic liquid until a depleted flow one (substantially or predominantly plasma) is generated at outlet 350.

Not separately illustrated in FIG. 3, an additional holographic trapping separation stage may also be utilized to aid in the separation of these blood fractions. For example, a holographic trapping separation stage may be utilized in lieu of, or in addition to, second stage 310. In addition, while the second stage separation has been illustrated using flow one, in other embodiments, flow two may be subjected to a second (or more) stage separation, in addition to or in lieu of the additional separation stage of flow one. Moreover, additional separation stages may be utilized in series or in parallel.

Exemplary separations for blood sorting include: (a) separation of one or more blood cell types from some or all of the other blood cell types and/or from the blood plasma or fluid medium by sedimentation rate zonal separation; (b) separation as in (a) but with isopycnic separation; (c) removal of just the red blood cells (RBCs) or the RBCs and white blood cells (WBCs) from the solution by sedimentation; (d) concentration of the platelets from the plasma using sedimentation; (e) extraction of the RBCs using dielectrophoresis, electrophoresis, or magnetic separation; (f) concentration or extraction of platelets from a solution using optical techniques including optical tweezers and optical fractionation; and (g) separation of blood components using agents which may bind to a particular cell type (such as functionalized beads) and be acted upon by any of the above separation techniques, after which the agent may or may not be unbound from the cell type.

For blood sorting, a combined approach may be the most effective, such as: first extract most of the RBCs and WBCs using sedimentation rate zonal separation, then extraction and concentration of the platelets using optical fractionation, discussed below. The optical fractionation step will act not only to concentrate the platelets (which could also, for example, be done by a centrifugation step at the end), but will provide a second step which will exert strong suppression on the WBCs accidentally collected with the platelets, for the example of platelet aphoresis. Such concentration steps may also include filtering, such as to filter WBC from a platelet fraction or a plasma fraction.

Cell "washing" is also a significant application of the apparatus 100, 200 or 300. Such washing may include a change of media, for storage, preservation, or other medical purposes. Such washing may also consist of removing a media containing contaminants such as bacteria, by separating the cells of interest into another media flow free of such contamination.

Portions of, or outputs from, the sorting device 100, 200 or 300 may be inspected optically. This may be direct visual imaging, such as with a camera, utilizing direct bright-light imaging or fluorescent imaging. Or, it may be more sophisticated techniques such as spectroscopy, transmission spectroscopy, spectral imaging, or scattering such as dynamic light scattering or diffusive wave spectroscopy. In many cases, these inspection regions may be incorporated directly into the flow device to characterize the inputs, outputs, or intermediate steps. They may be for diagnostics or record-keeping, or they may be used to inform the overall process, such as for feedback on how processing is done or on the speed of flow or amount of each solution to use. In some cases, the optical inspection regions may be used in conjunction with additives, such as chemicals which bind to or affect parts of the solution or beads which are functionalized to bind and/or fluoresce in the presence of certain materials or diseases. For the example of blood sorting, these techniques may be used to measure cell concentrations, to detect disease, or to detect other parameters which characterize the blood.

Portions of, or outputs from, the sorting device 100, 200 or 300 also may be characterized electronically. For example, a portion of the sorting device may have electronic devices embedded. Example electronic devices may include: (a) capacitors, (b) electronic flow meters, (c) resistance meters for determining the bulk conductivity of the fluid, from which concentrations or compositions may be measured, or (d) pH measuring devices. For the application of blood sorting, measurements of cell concentration, iron content, flow rates, total cell counts, electrolyte concentration, pH, and other parameters may be a valuable part of a sorting device.

The flow components of the sorting device 100, 200 or 300 may be passive, being completely controlled externally by the flow rates of the inputs and outputs. Alternatively, there may be active flow components embedded in the device (not separately illustrated), such as valves which may be partially or fully opened or closed using electronic, optical, thermal, mechanical, or other influence. For the application of blood sorting, the sorting device 100, 200 or 300 may have an integrated method for storing and/or delivering one or more solutions. For example, a consumable sorting device may be manufactured to have a deformable membrane on a side of a reservoir. This reservoir may be filled with a solution, such as a buffering agent which is biologically compatible with the patient and which may be used to dilute the blood. Another example is that it could be filled with an anti-coagulant. The delivery and/or use of one such fluid may be actively controlled by mechanical influence, pressing on the membrane to deliver the fluid. Alternately, another mechanism may be used to deliver the fluid. Of particular interest, for the sake of simplicity and cost-saving, is the integration of various fluid solutions needed at differing steps in the sorting. Integrating these components may result in substantial simplification and reduction of the total cost of ownership and operation. It may also reduce the risk of contamination and error.

The device 100, 200 or 300 may include areas (not separately illustrated) where biological or chemical investigation of one or more of the fluids or fluid components. This may include measurements of pH, the presence of certain biological or chemical materials, or other measurements. For the application of blood sorting, this may include detection of disease, characterization of concentrations of various cell types or materials in the plasma, characterization of iron content, determination of blood type, or other evaluation of blood quality, type, or category.

The device 100, 200 or 300 may include a region (not separately illustrated) which sterilizes the solution using optical methods, such as exposure to UV light, or other methods. The sterilization may act upon solutions which are initially part of the device or added to it for buffering, washing, diluting, or other impacts on the sample solution. Or, the sterilization may act upon part or all of the sample solution being processed. For the application of blood sorting, optical sterilization of the solutions used in the device other than whole blood may be important. Also, sterilization of the blood or certain fractions of the blood may be important.

The device 100, 200 or 300 may be comprised of materials such that one or more surfaces have been constructed so as to interact physically or chemically with certain materials. For example, a surface may be functionalized so that certain materials adhere to it, for the purpose of extracting these materials from the solution or for the purpose of diagnostics. For the application of blood sorting, functionalized surfaces may be used to extract unwanted materials from certain fractions. Alternately, they may be used to collect materials which are at low concentration for the purpose of measuring the degree to which a material or a type of material is present, such as for disease detection.

The sorting device 100, 200 or 300 may contain regions where sorting acts in parallel but without physical walls to separate the flows. For example, a parallel sorting region may have multiple inlets 120 and outlets 130, some of which are functionally similar to each other. Instead of having physical dividers distinguishing the multiple parallel sorters, the division occurs as a consequence of the physical properties of the solutions and the flow. The contacting parallelized sorters regions may yield high sorting rates with more simple and cheap devices. They may also act to avoid contact with surfaces. For blood sorting, these regions would be used to minimize contact with surfaces and to maximize sorting rate while reducing costs and complexity.

The device 100, 200 or 300 may have regions which are designed to regulate flow rate or the flow character (not separately illustrated). For example, in many cases laminar flow is required, and often a particular flow profile is desired. In other cases, several regions of the device should have identical flow rates and behavior. For these reasons, areas with shapes and other properties to influence flow behavior are often needed. In some cases, this is done by making very symmetric flow designs. In other cases, large changes in the diameter of flow regions and/or the existence of reservoirs help to maintain uniform flow rates. In other cases, very carefully designed channels provide the exact balancing of flow rates needed. To maintain laminar flow, areas where slow changes in channel size occur may be important. Obstacles or dividers may also act to maintain laminar flow. For blood sorting, flow regulation is important to achieve high sorting rates while maintaining the yield and purity of the fractions.

Not separately illustrated, the device 100, 200 or 300 may contain regions which are designed for mechanical mixing of the fluids, such as regions which encourage turbulence. For example, a region with a fast narrow stream entering a region with a large dimension may produce turbulent flow and mixing. For blood sorting, a mixing region may mix a diluent or anticoagulant with the blood, or may mix other solutions together as needed.

The device 100, 200 or 300 may contain regions which align cells or materials in a certain way (not separately illustrated). This is sometimes done through shear flows, but may also be done by imposing external fields such as electric fields.

The device 100, 200 or 300 may contain regions designed to lyse cells or break up materials (not separately illustrated). This may be done through shear flows, vibration, forcing through an orifice, electrical, or other means. For blood sorting, this may be valuable for the elimination of certain cell types or aggregates which may form. It may also be valuable for diagnostic purposes, such as disease detection or measurement of parameters which pertain to the contents of cells.

The device may contain regions (not separately illustrated) which swell or dehydrate cells or objects, such as by introducing agents which change the osmotic pressure or by changing the physical pressure. This may be done, for example, as a step prior to isopycnic sorting to adjust the density of the cells or objects. It may also be done to kill or shock certain components. For the example of blood sorting, this may be done as a later stage purification step to remove or neutralize undesired components.

The device 100, 200 or 300 may contain regions which heat or cool one or more solutions (not separately illustrated). This may be done for its impact on physical properties, such as viscosity or density. Or, it may be done for its impact on chemical properties, such as chemical reaction rates or chemical stability. Or, it may be done for its impact on biological properties, such as motility, metabolism rate, or viability. Also, it may be done for system-level compatibility, such as in preparation for the following processing step. For the example of blood sorting, solutions which are returned to the patient may be maintained at an appropriate temperature to avoid chilling the patient. Solutions which are to be stored may be cooled during processing to preserve those fractions or prepare them for the next processing or storage step.

The device 100, 200 or 300 may contain reservoirs which serve to store solutions which will be used during the process run, or which may be generated during the process run (not separately illustrated). Having these reservoirs integral to the sorting device simplifies the use of the device and reduces the need for additional parts. For the example of blood sorting, reservoirs may contain anticoagulants, diluents, dilutants, and any other solutions needed in the process. Reservoirs may also be incorporated which will hold the sorted fractions or waste fractions.

The device 100, 200 or 300 may contain regions which enhance mixing by diffusion (not separately illustrated). For example, when mixing by contacting two laminar flows, parallelizing into many narrow contacting flows enhances the overall mixing rate by diffusion. For the example of blood sorting, diffusive mixing regions may be used to mix diluent, anticoagulant, or other solutions with whole blood or blood fractions.

Also not separately illustrated, the device may contain regions with bubble traps to remove air bubbles from the system. This may be done by having a region where air bubbles are able to rise from a region with flow to a region above the primary flow region. For the example of blood sorting, this may be done in a simple way to guarantee that small air bubbles from the loading or running of the system do not pass on to the patient or the collection samples.

As indicated above, the device 100, 200 or 300 may contain regions which act to suppress any pulsation in the flow (not separately illustrated), such as that which occurs when peristaltic pumps are used. One way to suppress pulsation is to incorporate a "bubble-trap" into the device. The presence of an air pocket, which is in contact with the fluid, allows for compression of the air pocket as pressure in the fluid increases and decreases. Thus, the air pocket acts as a shock absorber, smoothing out the flow. Other devices may be used as well, such as a flexible membrane which may bend under higher pressures, thereby smoothing out the pressure and flow rate. For the application of blood sorting, pulsation reduction regions will yield more precise and smooth flows, and therefore higher sorting rates, purity, and yield.

The device 100, 200 or 300 may contain regions which reveal the state of the device (not separately illustrated). For a consumable, it may indicate whether the device has been sterilized or whether it has been used. For the application of blood sorting, one would want indicators to confirm both that the sorting device has been sterilized and that the device has not yet been used or contaminated.

The sorting device 100, 200 or 300, or overall sorting system, may contain mechanisms for precise leveling of the flow sorter. This is important because for some sorters, buoyant forces may cause unintentional flows and have negative impacts on sorting yields and purity in cases where the device is not precisely leveled. Additionally, the sorting device may contain components which reveal whether it is well-balanced, or the degree to which it is balanced. For example, it may have an electronic or gravity-based balance incorporated in the sorting device itself. One example of such a device is a shaped channel with fluid and an air bubble in it. The position of the air bubble may reveal the angle of the tilt of the device. Another such device may use a metal ball in a track to reveal the tilt angle. Another manifestation is to use an optical alignment, such as bouncing a light source off a surface or passing a light source through a wedge to identify its orientation. For the application of blood sorting, leveling controls and indicators are significant to guarantee high-yield and high-purity products.

The sorting device 100, 200 or 300, or overall sorting system, may contain mechanisms for maintaining uniform and/or constant temperatures of the device and/or the solution (not separately illustrated). This is important to eliminate thermally-induced buoyant forces which may cause unintentional flows and have negative impacts on sorting yields and purity. Additionally, the sorting device may have indicators in it, or in the sorting system as a whole, which indicate the temperature and/or temperature uniformity of one or more components. For the application of blood sorting, temperature uniformity controls and indicators may be significant to guarantee high-yield and high-purity products.

The sorting device 100, 200 or 300, or overall sorting system, may contain mechanisms for measuring the level and concentration of one or more input or output solution (not separately illustrated). These measurements may be used to gauge the speed of operation, completion time, error state, for general monitoring, or for other applications. For the application of blood sorting, level and concentration indicators may be used to identify when sufficient sample has been collected or to detect when a failure or depletion of a solution has occurred.

Lastly, the sorting device 100, 200 or 300, or overall sorting system, may have a method for priming the system with one or more fluids using standard bottom-up filling or evacuation. Purging may similarly be done by draining the device or by flowing a solution through it. At the early stages of a sorting run, the priming solution may be discarded until a time when the priming solution has been mostly exhausted and the desired solution is obtained. Similarly, at the late stages of a sorting run, a fluid may be used to push the sorted material through the system to minimize waste and maximize yield.

Figure 4:
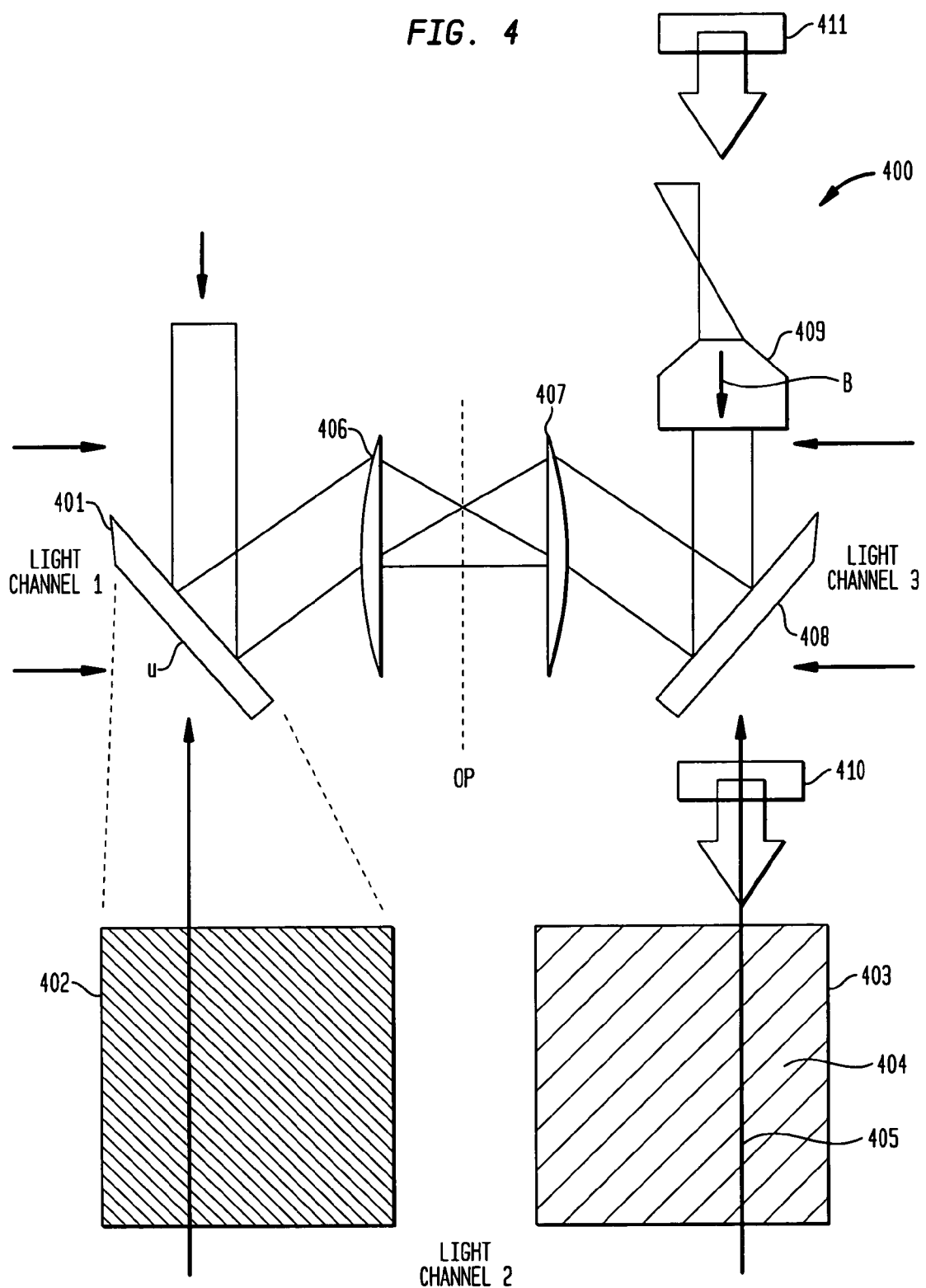
FIG. 4 schematically illustrates a holographic optical trapping system according to one embodiment consistent with the present invention.

FIG. 4 schematically illustrates a holographic optical trapping system 400, generally used in conjunction with an apparatus 100, 200 or 300, according to one embodiment consistent with the present invention. Additional detail concerning holographic optical trapping is available in the first related application. In a holographic optical trapping apparatus or system 400 as illustrated in FIG. 4, light is incident from a laser system, and enters as shown by the downward arrow, to power the system 400.

A phase patterning optical element 401 is preferably a dynamic optical element (DOE), with a dynamic surface, which is also a phase-only spatial light modulator (SLM) such as the "PAL-SLM series X7665," manufactured by Hamamatsu of Japan, the "SLM 512SA7" or the "SLM 512SA15" both manufactured by Boulder Nonlinear Systems of Lafayette, Colo. These dynamic phase patterned optical elements 401 are computer-controlled to generate beamlets by a hologram encoded in the medium which may be varied to generate the beamlets and select the form of the beamlets. A phase pattern 402 generated on the lower left of FIG. 4 produces the traps 403 shown in the lower right filled with 1 μm diameter silica spheres 404 suspended in water 405. Thus, the system 400 is controlled by the dynamic hologram shown below on the left.

The laser beam travels through lenses 406, 407, to dichroic mirror 408. The beam splitter 408 is constructed of a dichroic mirror, a photonic band gap mirror, omni directional mirror, or other similar device. The beam splitter 408 selectively reflects the wavelength of light used to form the optical traps 403 and transmits other wavelengths. The portion of light reflected from the area of the beam splitter 408 is then passed through an area of an encoded phase patterning optical element disposed substantially in a plane conjugate to a planar back aperture of a focusing (objective) lens 409.

In single beam optical trapping (also called laser or optical tweezers) it had been thought, prior to the invention of the first related application, that a high numerical aperture lens was necessary for acceptable optical traps. A basis for this thinking was that, for optical trapping, one uses the gradient in the electric field of the impinging light to trap the particle. In order to have a large trapping force it has been thought necessary to have a large gradient in the electric field (or number density of rays). The way that one usually accomplishes this is to pass the light field through a high numerical aperture lens.

A concern with observation and trapping of samples within a large field of view is that such observation and trapping would involve an objective lens with a low numerical aperture. Contrary to prior teaching, the invention of the first related application provides a low numerical aperture lens as, for example, the objective lens 409 in FIG. 4. The ability to observe and trap in this situation could be useful in any application where one would benefit from a large field of view given by a low magnification lens, such as placing microscopic manufactured parts or working with large numbers of objects, such as cells, for example.

Suitable phase patterning optical elements are characterized as transmissive or reflective depending on how they direct the focused beam of light or other source of energy. Transmissive diffractive optical elements transmit the beam of light or other source of energy, while reflective diffractive optical elements reflect the beam.

The phase patterning optical element 401 may also be categorized as having a static or a dynamic surface. Examples of suitable static phase patterning optical elements include those with one or more fixed surface regions, such as gratings, including diffraction gratings, reflective gratings, and transmissive gratings, holograms, including polychromatic holograms, stencils, light shaping holographic filters, polychromatic holograms, lenses, mirrors, prisms, waveplates and the like. The static, transmissive phase patterning optical element is characterized by a fixed surface.

In some embodiments, however, the phase patterning optical element 401 itself is movable, thereby allowing for the selection of one more of the fixed surface regions by moving the phase patterning optical element 401 relative to the laser beam to select the appropriate region.

The static phase patterning optical element may be attached to a spindle and rotated with a controlled electric motor (not shown). The static phase patterning optical element has a fixed surface and discrete regions. In other embodiments of static phase patterning optical elements, either transmissive or reflective, the fixed surface has a non-homogeneous surface containing substantially continuously varying regions, or a combination of discrete regions, and substantially continuously varying regions.

Examples of suitable dynamic phase patterning optical elements having a time dependent aspect to their function include computer-generated diffractive patterns, phase-shifting materials, liquid crystal phase-shifting arrays, micromirror arrays, including piston mode micro-mirror arrays, spatial light modulators, electro-optic deflectors, accousto-optic modulators, deformable mirrors, reflective MEMS arrays and the like. With a dynamic phase patterning optical element 401, the medium 405 which comprises the phase patterning optical element 401 encodes a hologram which may be altered, to impart a patterned phase shift to the focused beam of light which results in a corresponding change in the phase profile of the focused beam of light, such as diffraction, or convergence. Additionally, the medium 405 may be altered to produce a change in the location of the optical traps 403. It is an advantage of dynamic phase patterning optical elements 401, that the medium 405 may be altered to independently move each optical trap 403. In those embodiments in which the phase profile of the beamlets is less intense at the periphery and more intense at regions inward from the periphery, overfilling the back aperture by less than about 15 percent is useful to form optical traps with greater intensity at the periphery, than optical traps formed without overfilling the back aperture.

In some embodiments, the form of an optical trap may be changed from its original form to that of a point optical trap, an optical vortex, Bessel beam, an optical bottle, an optical rotator or a light cage The optical trap may be moved in two or three dimensions. The phase patterning optical element is also useful to impart a particular topological mode to the laser light, for example, by converting a Gaussian into a Gauss-Laguerre mode. Accordingly, one beamlet may be formed into a Gauss-Laguerre mode while another beamlet may be formed in a Gaussian mode. The utilization of Gauss-Laguerre modes greatly enhances trapping by reducing radiation pressure.

Figure 5:
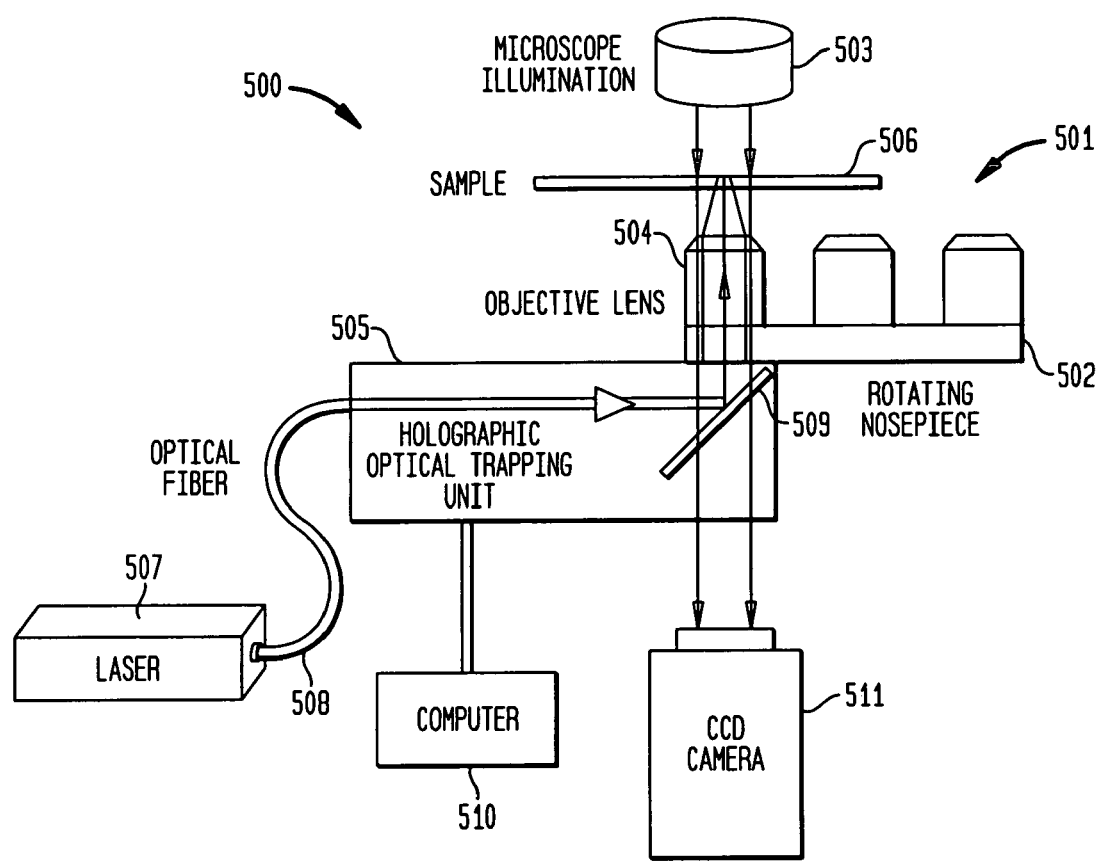
FIG. 5 is a schematic diagram of a holographic optical trapping system for sorting objects according to one embodiment in accordance with the present invention.

FIG. 5 is a schematic diagram of a holographic optical trapping system for sorting objects, and is used in conjunction with an apparatus 100, 200 or 300, according to one embodiment in accordance with the present invention. In one such embodiment, an optical trapping system 500 (see FIG. 5) (such as the BioRyx system sold by Arryx, Inc., Chicago, Ill.) includes a Nixon TE 2000 series microscope 501 into which a mount for forming the optical traps using a holographic optical trapping unit 505 has been placed. The nosepiece 502 to which is attached a housing, fits directly into the microscope 501 via the mount. For imaging, an illumination source 503 is provided above the objective lens 504 to illuminate the sample 506. In accordance with the present invention, the sample 506 is one of the separation stages of the apparatus 100, 200 or 300.

In one embodiment, the optical trap system 400 (see FIGS. 4 and 5) includes one end of the first light channel which is in close proximity to the optical element, and the other end of the first light channel which intersects with and communicates with a second light channel formed perpendicular thereto. The second light channel is formed within a base of a microscope lens mounting turret or "nosepiece". The nosepiece is adapted to fit into a Nixon TE 200 series microscope. The second light channel communicates with a third light channel which is also perpendicular to the second light channel. The third light channel traverses from the top surface of the nosepiece through the base of the nosepiece and is parallel to an objective lens focusing lens 409. The focusing lens 409 has a top and a bottom forming a back aperture. Interposed in the third light channel between the second light channel and the back aperture of the focusing lens is a dichroic mirror beam splitter 408.

Other components within the optical trap system for forming the optical traps include a first mirror, which reflects the beamlets emanating from the phase patterning optical element 401 through the first light channel, a first set of transfer optics 406 disposed within the first light channel, aligned to receive the beamlets reflected by the first mirror, a second set of transfer optics 407 disposed within the first light channel, aligned to receive the beamlets passing through the first set of transfer lenses, and a second mirror 408, positioned at the intersection of the first light channel and the second light channel, aligned to reflect beamlets passing through the second set of transfer optics and through the third light channel.

To generate the optical traps, a laser beam is directed from a laser 507 (see FIG. 5) through a collimator and through an optical fiber end 508 and reflected off the dynamic surface of the diffractive optical element 509. The beam of light exiting the collimator end of the optical fiber is diffracted by the dynamic surface of the diffractive optical element into a plurality of beamlets. The number, type and direction of each beamlet may be controlled and varied by altering the hologram encoded in the dynamic surface medium. The beamlets then reflect off the first mirror through the first set of transfer optics down the first light channel through the second set of transfer optics to the second mirror; and are directed at the dichroic mirror 509 up to the back aperture of the objective lens 504, are converged through the objective lens 504, thereby producing the optical gradient conditions necessary to form the optical traps. That portion of the light which is split through the dichroic mirror 509, for imaging, passes through the lower portion of the third light channel forming an optical data stream (see FIG. 4).

Spectroscopy of a sample of biological material may be accomplished with an imaging illumination source 503 suitable for either spectroscopy or polarized light back scattering, the former being useful for assessing chemical identity, and the later being suited for measuring dimensions of internal structures such as the nucleus size. Using such spectroscopic methods, in some embodiments, cells are interrogated. A computer 510 may be used to analyze the spectral data and to identify cells bearing either an X or Y chromosome, or a suspected cancerous, pre-cancerous and/or non-cancerous cell types, or identify various types of blood cells, for example. The computer program then may apply the information to direct optical traps to contain selected cell types. The contained cells then may be identified based on the reaction or binding of the contained cells with chemicals.

The present method and system lends itself to a semi-automated or automated process for tracking the movement and contents of each optical trap. The movement may be monitored, via video camera 511, spectrum, or an optical data stream and which provides a computer program controlling the selection of cells and generation of optical traps.

In other embodiments, the movement of cells is tracked based on predetermined movement of each optical trap caused by encoding the phase patterning optical element. Additionally, in some embodiments, a computer program is used to maintain a record of each cell contained in each optical trap.

The optical data stream may then be viewed, converted to a video signal, monitored, or analyzed by visual inspection of an operator, spectroscopically, and/or video monitoring. The optical data stream may also be processed by a photodetector to monitor intensity, or any suitable device to convert the optical data stream to a digital data stream adapted for use by a computer.

In an approach which does not employ an SLM, movement is accomplished by transferring the objects from a first set of optical traps to a second, third, and then fourth etc. To move the objects from the first position to a second position, a static phase patterning optical element is rotated around a spindle to align the laser beam with a second region which generates the second set of optical traps at a corresponding second set of predetermined positions. By constructing the second set of optical traps in the appropriate proximity to the first position, the probes may be passed from the first set of optical traps to the second set of optical traps. The sequence may continue passing the probes from the second set of predetermined positions to a third set of predetermined positions, from the third set of positions to a fourth set of predetermined positions, and from the fourth set of predetermined positions and so forth by the rotation of the phase patterning optical element to align the appropriate region corresponding to the desired position. The time interval between the termination of one set of optical traps and the generation of the next is of a duration to ensure that the probes are transferred to the next set of optical traps before they drift away.

In a staggered movement of the objects from a wide to narrow proximity the staggered movement of the cells occurs in a similar fashion. However, as the objects are passed from a first set of optical traps to a second set and moved to second and subsequent positions, the staggered arrangement of the traps allows the objects to be packed densely without placing a set of traps in too close a proximity to two objects at the same time which could cause the objects to be contained by the wrong optical trap Once an object or cell has interacted with a trap, spectral methods may be used to investigate the cell. The spectrum of those cells which had positive results (i.e., those cells which reacted with or bonded with a label) may be obtained by using imaging illumination such as that suitable for either inelastic spectroscopy or polarized light back scattering. A computer may analyze the spectral data to identify the desired targets and direct the phase patterning optical element to segregate those desired targets. Upon completion of the assay, selection may be made, via computer and/or operator, of which cells to discard and which to collect.

As a consequence, in accordance with the present invention, the plurality of holographic optical traps, which are capable of being independently manipulated, can be utilized in conjunction with an apparatus 100, 200 or 300, to manipulate components or particles, such as blood cells and other blood components, from one flow to another flow, as part of a separation stage. For example, components of interest in flow one may be identified and moved by the holographic optical traps into flow two, and thereby separated from the other components of flow one.

FIG. 6 is a flow diagram illustrating a method embodiment of the present invention, and provides a useful summary. Beginning with start step 600, the method provides a first flow having a plurality of components, step 605, such as a plurality of blood components. A second flow is provided, step 610, and the first flow is contacted with the second flow to provide a first separation region, step 615. A first component of the plurality of components is differentially sedimented into the second flow, step 620, while a second component of the plurality of components is concurrently maintained in the first flow, step 625. The second flow having the first component is differentially removed from the first flow having the second component, step 630. When no additional separations (or stages) are to occur, step 635, the method may end, return step 680.

When an additional separation is to occur, step 635, the method proceeds to step 640, and a third flow is provided. The first flow is contacted with the third flow to provide a second separation region, step 645. When holographic manipulation is to be utilized in the second, additional separation, step 650, the method proceeds to step 655, and a plurality of holographic traps are generated, typically using optical wavelengths. Using the holographic traps, the second component of the plurality of components is differentially moved into the third flow, step 660. When holographic manipulation is not to be utilized in the second, additional separation, step 650, the method proceeds to step 665, and the second component of the plurality of components is differentially sedimented into the third flow. Following either step 660 or 665, a third component of the plurality of components is concurrently maintained in the first flow, step 670. The third flow having the second component is then differentially removed from the first flow having the third component, step 675, and the method may end, return step 680. While not separately illustrated in FIG. 6, it should be understood that the method may continue for additional separation stages, such as a third fourth, fifth, and so on.

Also in summary, and by way of example, the first component of the plurality of components may be a plurality of red blood cells and a plurality of white blood cells, while the second component is a plurality of platelets. In the second separation, the plurality of white blood cells may be holographically separated from the plurality of red blood cells, using techniques such as holographic (optical) trapping. Holographic trapping may also be utilized to holographically remove a plurality of contaminants from the first flow, or to holographically separate biological debris from the first flow. In the various embodiments, the first flow may substantially comprise whole blood from a donor and an anticoagulant, and the second flow may substantially comprise plasma from the donor. The various sedimentation steps may be rate zonal or isopycnic. The various flows are substantially non-turbulent, and may also be substantially laminar.

The first and second separation regions each have a predetermined length substantially parallel to a direction of flow and a predetermined depth substantially perpendicular to the direction of flow, the predetermined length and predetermined depth having been determined from a first sedimentation rate of the first component, from a second sedimentation rate of the second component, from a first flow rate of the first flow, and from a second flow rate of the second flow. The first flow and the second flow may have substantially the same flow rates. Alternatively, the first flow may have a first flow rate and the second flow may have a second flow rate, in which the second flow rate is comparatively greater than the first flow rate.

Also in summary, the present invention further provides an apparatus for separating a fluid mixture into constituent, non-motile components, including: (1) a first sorting channel (110 or 325) having a first inlet (120 or 315) for a first flow and a second inlet (120 or 320) for a second flow; the first sorting channel further having a first outlet (130 or the continuous channel of FIG. 3) for the first flow and a second outlet 130 (or 330) for the second flow, the first sorting channel adapted to allow a first component in the first flow, of a plurality of components in the first flow, to sediment into the second flow to form an enriched second flow and a depleted first flow, while concurrently maintaining a second component of the plurality of components in the first flow; (2) a second, optically transparent sorting channel (110 or 340) having a first optical inlet coupled to the first outlet (the continuous channel of FIG. 3) for the first flow and having a first optical outlet (350), the second, optically transparent sorting channel further having a second optical inlet (335) for a third flow and a second optical outlet for the third flow (345); and (3) a holographic optical trap system (400, 500) coupled to the second, optically transparent sorting channel, the holographic optical trap system adapted to generate a holographic optical trap to select and move the second component from the first flow into the third flow.

Another apparatus or system for separating a plurality of components in a fluid comprises: an optically transparent sorting channel 100, 200 or 300 having a first inlet for a first flow and a second inlet for a second flow, the optically transparent sorting channel further having a first outlet for the first flow and a second outlet for the second flow; and a holographic optical trap system coupled to the optically transparent sorting channel, the holographic optical trap system 500 adapted to generate a holographic optical trap to select and move a first component in the first flow, of a plurality of components in the first flow, into the second flow to form an enriched second flow and a depleted first flow, while a second component of the plurality of components is concurrently maintained in the first flow.

Lastly, another method embodiment provides for separating a plurality of cells, comprising: providing a first flow having the plurality of cells; providing a second flow; contacting the first flow with the second flow to provide a first separation region; and differentially sedimenting a first cell of the plurality of cells into the second flow while concurrently maintaining a second cell of the plurality of cells in the first flow. The method generally also includes differentially removing the second flow having the first cell from the first flow having the second cell. The method may also provide for providing a third flow; contacting the first flow with the third flow to provide a second separation region; and differentially sedimenting the second cell of the plurality of cells into the third flow while concurrently maintaining a third cell of the plurality of cells in the first flow. In addition, a plurality of second cells may be holographically separated from the first flow, and a plurality of contaminants or biological debris may be holographically removed from the first flow.

While discussion above has focused on the sorting of blood components to create different blood fractions, the apparatus, methods and systems of the present invention may be extended to other types of particulate, biological or cellular matter which are non-motile, which are capable of sedimenting or creaming within a fluid flow, or which are capable of being manipulated optically. For example, the methodology of the present invention could be utilized to separate non-motile or non-viable sperm cells from viable cells, by allowing the non-motile cells to sediment from a first flow into a second flow. Other sorts of cell separation may also be performed, such as separating islet cells from other types of pancreatic cells, or otherwise separating islet cell clusters of different sizes, through either or both flow separation or optical tweezing (trapping). Viruses, proteins and other large molecules having different sedimentation rates may also be separated with the present invention. The holographic optical trapping utilized with the various separation stages may also be particularly useful in these other types of cell or particle separations.

From the foregoing, it will be observed that numerous variations and modifications may be effected without departing from the spirit and scope of the novel concept of the invention. It is to be understood that no limitation with respect to the specific methods and apparatus illustrated herein is intended or should be inferred. It is, of course, intended to cover by the appended claims all such modifications as fall within the scope of the claims.

The invention claimed is:

1. A method of separating a fluid mixture into constituent, non-motile components, the method comprising:
   providing a substantially laminar first flow having the fluid mixture, the fluid mixture having a plurality of components, the plurality of components having a corresponding plurality of sedimentation rates;
   providing a substantially laminar second flow;
   contacting the first flow with the second flow to provide a first separation region, the first flow and the second flow having a substantially non-turbulent interface within the separation region;
   differentially sedimenting from the first flow a first component of the plurality of components into the second flow to form an enriched second flow and a depleted first flow, while concurrently maintaining a second component of the plurality of components in the first flow, the first component having a first sedimentation rate of the plurality of sedimentation rates and the second component having a second sedimentation rate of the plurality of sedimentation rates, wherein the first sedimentation rate is comparatively greater than the second sedimentation rate;
   differentially removing the enriched second flow from the depleted first flow; and holographically manipulating the second component in the depleted first flow.

2. The method of claim 1, wherein the fluid mixture is whole blood, wherein the first component is a plurality of red blood cells and white blood cells, and wherein the second component is a plurality of platelets.

3. The method of claim 1, wherein the optical manipulation step further comprises:
   holographically trapping the second component to remove the second component from the depleted first flow.

4. The method of claim 1, further comprising:
   holographically removing a plurality of contaminants or biological debris from the first flow.

5. The method of claim 1, further comprising:
   providing a third flow;
   contacting the depleted first flow with the third flow to provide a second separation region; and
   holographically trapping the second component and moving the second component from the depleted first flow into the third flow while concurrently maintaining a third component of the plurality of components in the depleted first flow.

6. The method of claim 4, further comprising: recirculating the depleted first flow to form the second flow.

* * * * *